United States Patent
Chun et al.

(10) Patent No.: US 9,623,149 B2
(45) Date of Patent: Apr. 18, 2017

(54) METHOD FOR PRODUCING AN ACELLULAR DERMAL MATRIX, AND ACELLULAR DERMAL MATRIX PRODUCED BY SAME

(75) Inventors: Wook Chun, Seoul (KR); Weon Ik Choi, Seongnam (KR); Joon Pio Hong, Seongnam (KR); Hyun Seung Ryu, Yongin (KR)

(73) Assignee: CGBio Co., Ltd., Kyunggi-Do (KR)

( * ) Notice: Subject to any disclaimer, the term of this patent is extended or adjusted under 35 U.S.C. 154(b) by 0 days.

(21) Appl. No.: 13/580,248

(22) PCT Filed: Jun. 11, 2010

(86) PCT No.: PCT/KR2010/003783
§ 371 (c)(1),
(2), (4) Date: Aug. 21, 2012

(87) PCT Pub. No.: WO2011/105663
PCT Pub. Date: Sep. 1, 2011

(65) Prior Publication Data
US 2012/0329034 A1    Dec. 27, 2012

(30) Foreign Application Priority Data
Feb. 26, 2010 (KR) .................. 10-2010-0018134

(51) Int. Cl.
*A61L 27/36* (2006.01)
*A61L 27/60* (2006.01)

(52) U.S. Cl.
CPC ......... *A61L 27/362* (2013.01); *A61L 27/3687* (2013.01); *A61L 27/60* (2013.01); *A61L 2430/40* (2013.01)

(58) Field of Classification Search
CPC ..................................................... A61L 27/362
(Continued)

(56) References Cited

U.S. PATENT DOCUMENTS

| 5,336,616 A | 8/1994 | Livesey et al. |
| 5,891,617 A * | 4/1999 | Watson ............... A01N 1/02 424/571 |

(Continued)

FOREIGN PATENT DOCUMENTS

| KR | 10-2003-0060767 | 7/2003 |
| KR | 10-2004-0090033 | 10/2004 |

(Continued)

OTHER PUBLICATIONS

Reagan et al., Analysis of Cellular and Decellular Allogeneic Dermal Grafts for the Treatment of Full-Thickness Wounds in Porcine Model, 1997, The Journal of Trauma: Injury, Infection, and Critical Care 43(3): 458-466.*

(Continued)

*Primary Examiner* — Sharmila G. Landau
*Assistant Examiner* — Stephanie McNeil
(74) *Attorney, Agent, or Firm* — Fennemore Craig, P.C.

(57) ABSTRACT

The present invention relates to a method for producing an acellular dermal matrix, and to an acellular dermal matrix produced by same, and more particularly, to a method for producing an acellular dermal matrix, in which sucrose is added to base ingredients consisting of glycerol, propylene glycol, and a base solvent or solution so as to produce a cryoprotectant, the solution is injected into the skin below the epidermis and dermis from which cells have been removed, and freeze-drying is then performed.

5 Claims, 4 Drawing Sheets

(58) Field of Classification Search
USPC .......................................................... 435/1.3
See application file for complete search history.

(56) References Cited

U.S. PATENT DOCUMENTS

| | | | | |
|---|---|---|---|---|
| 6,740,484 | B1* | 5/2004 | Khirabadi et al. | 435/1.3 |
| 2002/0077697 | A1* | 6/2002 | Ranieri | A61F 2/062 |
| | | | | 623/1.41 |
| 2003/0096414 | A1* | 5/2003 | Ciccarone et al. | 435/383 |
| 2005/0222027 | A1* | 10/2005 | Chiang et al. | 514/12 |
| 2006/0210960 | A1* | 9/2006 | Livesey | A01N 1/00 |
| | | | | 435/2 |

FOREIGN PATENT DOCUMENTS

| KR | 10-2005-0039960 | 5/2005 |
|---|---|---|
| KR | 10-2005-0104704 | 11/2005 |

OTHER PUBLICATIONS

Isachenko et al, Ultrarapid Freezing of Rat Embryos with Rapid Dilution of Permeable Cryoprotectants, 1997, Cryobiology 34:157-164.*
Wu et al, Identification and Localization of Major Soluble Vitreous Proteins in Human Ocular Tissue, 2004, Am J Ophthalmol. 137(4):655-61.*
Waldman et al, Preservation of natural endothelial cytopathogenicity of cytomegalovirus by propagation in endothelial cells, 1991, Arch Virol 117: 143-164.*
PCT/KR2010/003783 International Search Report, 5 pages.
Applegate, L.A. et al., "Whole-Cell Bioprocessing of Human Fetal Cells for Tissue Engineering of Skin" Skin Pharmacol., Physiol., 2009, vol. 22, pp. 63-73.
Müller-Schweinitzer, E., et al., "Sucrose promotes the functional activity of blood vessels after cryopreservation in DMSO-containing fetal calf serum" Naunyn-Schmiedeberg's Arch. Pharmacol., 1992, vol. 345, pp. 594-597.

* cited by examiner

METHOD FOR PRODUCING AN ACELLULAR DERMAL MATRIX, AND ACELLULAR DERMAL MATRIX PRODUCED BY SAME

TECHNICAL FIELD

The present invention relates to a method for preparing an acellular dermal matrix (ADM) and an acellular dermal matrix prepared therefrom. More specifically, the present invention relates to a method in which a cryoprotectant is prepared by adding sucrose to basic constituents comprising glycerol, propylene glycol, and a basic solvent or solution, and the resulting solution is then penetrated into skin tissue in which epidermis and cells in dermis are removed to prepare an acellular dermal matrix.

BACKGROUND ART

Skin is the largest organ, covering the entire human body, and has functions of preventing loss of body fluid, influx of toxic substances and microbes from the outside, and protecting the body from physical and chemical stimuli. In the case of a patient whose skin is seriously impaired by severe burns, injury, carcinoma excision, skin diseases and the like, a protective membrane is needed to prevent infection of impaired regions and the loss of body fluid, along with not leaving a scar at the impaired region and preventing serious shrinkage accompanied by the process of spontaneous cure. For regenerating impaired skin tissue, there are three methods of autograft in which a patient's own skin is transplanted, allograft in which the skin of another human being is transplanted and xenograft in which the skin of an animal is transplanted. Among them, autograft is the most ideal. However, when burnt areas are extensive, there is a limitation of the regions from which skin tissue may be obtained, and the harvesting regions can leave a new scar. Allograft plays a greater role in helping the movement of cells at the periphery of the impaired region and curing than permanent engraftment.

Specifically, in the case of a third-degree burn in which epidermis, dermis and subcutaneous layers are impaired, skin grafting is essentially required. At present, autograft is most often used as skin grafting. However, harvesting autograft tissue creates a new injury, increasing patient's pain, time for complete recovery can be extended, and the economic burden is greater. In addition, when insufficient healthy regions remain—as with a severely burned patient—autograft cannot be applied, or grafting operations should be performed repeatedly. To resolve the above problems, allograft using the skin of another person and xenograft using the skin of an animal such as a pig have been tried. However, other side effects as well as immunorejection often result.

In the case of burn surgeries which are most generally performed in domestic and foreign hospitals, the dead epidermis and dermis layers are removed and skin grafting is then carried out by using an acellular dermis in which the epidermis and cells in the dermis are removed from skin harvested from a corpse to avoid immunorejection. Cultured keratinocytes will then complete the entire skin thereon. Because such a completed skin includes basement membrane, it can play a role in protecting the body from external hazardous substances.

U.S. Pat. No. 5,336,616 discloses a method for preparing collagen-based tissues for transplantation. However, tissues prepared according to the method disclosed in the above patent have problems in that cryoprotectant ingredients do not sufficiently penetrate into collagen tissues, and low concentration of sugar cannot sufficiently exclude moisture from collagen tissues—which has a characteristic of absorbing lots of moisture—so that many ice crystals are formed at the time of freezing. Such ice crystals make many pores in tissues in the course of drying and destroy collagen tissues, and the tissues are rapidly degraded after transplantation so as not to maintain their structure and to be absorbed.

DETAILED DESCRIPTION OF THE INVENTION

Technical Problem

Therefore, the technical problem to be solved in the present invention is to provide a new method for preparing an acellular dermal matrix which can efficiently increase tissue stability and minimize change of biological properties compared with conventional methods.

Solution to the Problem

To solve the above problems, the present invention provides a method for preparing an acellular dermal matrix comprising the steps of:
 i) removing epidermis of allograft skin;
 ii) removing cells in dermis;
 iii) mixing glycerol, propylene glycol and a basic solvent or solution;
 iv) dissolving sucrose in the solution to a final concentration of 20 to 40% by weight to obtain a cryoprotectant;
 v) penetrating the cryoprotectant into the skin from which epidermis and cells in dermis are removed; and
 vi) freeze-drying the cryoprotectant-penetrated skin.

The present invention also provides an acellular dermal matrix which is prepared by the above method.

Hereinafter, the present invention is described in detail.

In the present invention, epidermis and cells in dermis of allograft skin are removed to avoid immunorejection. The removal of epidermis and cells in dermis may be carried out according to various methods known in the art, and there is no special limitation thereto. The removal of epidermis may be carried out, for example, by treatment with enzymes such as trypsin, collagenase or dispase, or NaCl solution. The removal of cells in dermis may be carried out, for example, by treatment with Triton X100, Tween 20, Tween 40, Tween 60, Tween 80, SDS (sodium dodecylsulfate) and the like.

In the present invention, glycerol, propylene glycol, and a basic solvent or solution are used as basic constituents of a cryoprotectant. In the present invention, the basic solvent or solution refers to a solvent or solution which acts as a base for the preparation of the cryoprotectant, and distilled water, normal saline, a buffer solution which is used in treating animal cells or an animal cell culture medium may be used. In the present invention, the buffer solution—which is used in the treatment of animal cells—may be used without specific limitation. The example of the buffer solution includes, but is not limited to, PBS (phosphate-buffered saline), HBSS (Hank's balanced salt solution), TBS (Tris-buffered saline), TAPS (N-Tris(hydroxymethyl)methyl-3-aminopropanesulfonic acid) buffer, Bicine (N,N-Bis(2-hydroxyethyl)glycine) buffer, HEPES (4-(2-hydroxyethyl)-1-piperazineethanesulfonic acid) buffer, TES (N-Tris(hydroxymethyl)methyl-2-aminoethanesulfonic acid) buffer, PIPES (piperazine-N,N'-bis(2-ethanesulfonic acid)

buffer, cacodylate buffer, MES (2-(N-morpholino)ethanesulfonic acid) buffer and the like. In the present invention, the animal cell culture medium used may be any medium known in the art. In the present invention, the example of the animal cell culture medium includes, but is not limited to, MEM (Minimum Essential Media), DMEM (Dulbecco's Modified Eagle Media), RPMI 1640, IMDM (Iscove's Modified Dulbecco's Media), Defined Keratinocyte-SFM (without BPE (bovine pituitary extract)), Keratinocyte-SFN (with BPE), KnockOut D-MEM, AminoMAX-II Complete Medium and AminoMAX-C100 Complete Medium. In the present invention, glycerol, propylene glycol and the basic solvent or solution may be preferably used in a mixing ratio of 0.5~2: 0.5~2:6~10, more preferably 0.8~1.5:0.8~1.5:7~9, most preferably 1:1:8, based on weight. In the present invention, if the mixing ratio of glycerol and propylene glycol is less than 0.5, there may be a problem of freezing damage in a freezing step. If the mixing ratio of glycerol and propylene glycol is greater than 2, there may be a problem of the denaturation of tissue after freeze-drying.

In the present invention, a cryoprotectant is prepared by dissolving sucrose in the solution in which the basic constituents are mixed to the final concentration of 20 to 40% by weight. When freezing is carried out by using a slow freezing method, loss of moisture in cells and tissues can occur. As a result, ice crystals are formed in cells, and cells and tissues are physically destroyed by them. In addition, shrinkage of tissues caused by evaporation of moisture at the time of freeze-drying causes destruction of tissues—in which bondage of collagen fibers composing most of the tissue is weakened or disconnected by destroying tissues due to ice crystals—to be accelerated. The acellular dermal matrix prepared as such has weak tensile strength, so that it is difficult to expect good prognosis after surgery when it is transplanted at the joint sites of burn patients. As such, the maximum prevention of formation of ice crystals in tissues is the prerequisite of the cryoprotectant. In the present invention, glycerol having a property of membrane permeability, high concentration of sucrose and propylene glycol having a property of membrane impermeability are used as the major ingredients of cryopreservation solution to protect and stabilize tissues from physical destruction caused by ice crystals. In addition, propylene glycol used in the present invention is used as a food additive and in cosmetics since it shows little toxicity compared with other glycols, and has antibiotic activity to prevent proliferation of bacteria and fungi. Therefore, the cryoprotectant of the present invention can protect tissues from contamination after freeze-drying. As explained above, the stability of tissue of the acellular dermal matrix prepared according to the present invention can be improved. In addition, the optimal mixing ratio of sucrose, glycerol, propylene glycol, and the basic solvent or solution can further improve the stability of the dermal tissue. In the present invention, if the concentration of sucrose is less than 20% by weight, the stability of the tissue may be decreased due to ice crystals formed in a freezing step. If the concentration of sucrose is greater than 40% by weight, the stability of the tissue may be deteriorated by sugar crystals formed in the tissue after freeze-drying due to high concentration of sugar ingredients. In the present invention, the cryoprotectant is most preferably prepared by dissolving sucrose in the basic constituents-mixed solution to the final concentration of 30% by weight.

In the present invention, the penetration of the cryoprotectant into the skin from which epidermis and cells in dermis are removed may be carried out according to conventional methods known in the art. Preferably, the cryoprotectant may be penetrated into the skin tissue in a low-temperature bath. Because the sugar ingredient may be the cause of contamination as a nutrient source, it is preferable to treat a cryoprotectant at low temperature. In addition, because the treatment of cryoprotectant at room temperature may induce denaturation of collagen tissue which is a raw material, it is preferable to penetrate the cryoprotectant into the skin at low temperature rather than room temperature. Time needed for penetration may vary depending on the size of skin tissue and other factors. For example, the cryoprotectant may be penetrated into the skin tissue in a 4° C. low-temperature bath for about 6 to 24 hours.

In the present invention, it is preferable that the cryoprotectant-penetrated skin be frozen by using a freeze-dryer which can control the temperature rate. Use of a freeze-dryer that can control freezing rate allows the skin tissue to be frozen at a desired rate. In the present invention, the freezing rate of skin with the freeze-dryer that can control freezing rate is preferably −0.1° C. to −5° C. per minute, and most preferably −1° C. per minute.

Effects of the Invention

The acellular dermal matrix for transplantation prepared according to the processing method of the present invention shows that the stability of the tissue is high, extracellular matrix and basement membrane are well maintained without impairment, and the change of biological properties is minimized. As a result, the success rate of acellular dermal matrix grafting can be increased, and treatment duration can be curtailed.

DESCRIPTION OF EMBODIMENTS

Figure 1:
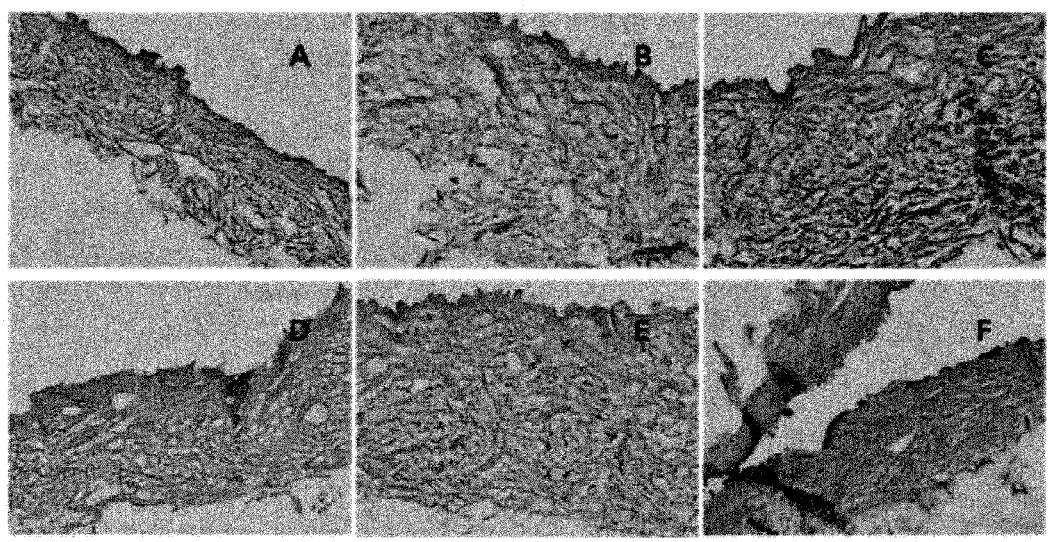
FIG. 1 is optical microscope photographs of acellular dermal matrix freeze-dried with a cryoprotectant using each concentration of sucrose after rehydration and H&E staining with 100× magnification. (A: 5% sucrose, B: 10% sucrose, C: 15% sucrose, D: 20% sucrose, E: 25% sucrose, F: 30% sucrose)

The present invention is explained in more detail with the following examples. However, it must be understood that the protection scope of the present invention is not limited to the example.

Because human skin tissue harvested from a donor (cadaver) is prohibited from being used in an experiment, pig skin—which is the closest to human skin—is used for preparing ten (10) of samples according to the following methods of Example and Comparative Examples.

EXAMPLE

An acellular dermal matrix was prepared with pig skin according to the following steps.
(1) Pig skin was washed with saline solution.
(2) The pig skin was cut at the size of 5×10 cm$^2$.
(3) The pig skin was immersed in 1M NaCl (Sigma, USA) solution.
(4) A 38° C. incubator (P-039, CoreTech, Korea) was prepared.
(5) The reaction of the pig skin immersed in 1M NaCl (Sigma, USA) solution was carried out in the 38° C. incubator with stirring for about 6 to 24 hours.
(6) Epidermis was removed by using forceps.
(7) The dermis from which the epidermis has been removed was washed with phosphate-buffered saline (pH 7.2, Gibco, USA).
(8) The washed dermis was immersed in 0.5% SDS and reacted with stirring at room temperature for 1 hour to remove cells from the dermis.
(9) The dermis from which cells have been removed was washed with phosphate-buffered saline.
(10) Glycerol (Sigma, USA), propylene glycol (Sigma, USA) and phosphate-buffered saline (Gibco, USA) were mixed in the weight ratio of 1:1:8.
(11) Sucrose (Sigma, USA) was added to the solution of step (10) as the final concentration of 30% by weight and dissolved to obtain a cryoprotectant.
(12) A low-temperature bath (P-039, CoreTech, Korea) was set at 4° C.
(13) The pig skin of step (9) was put in the 4° C. low-temperature bath, and then the cryoprotectant was penetrated into the pig skin for 12 hours.
(14) The penetration-completed pig skin was put in a Tyvek bag (Korea C&S Co., Ltd., Korea).
(15) A freezing dryer (Genesis 25XL, VirTis, USA) was prepared.
(16) The Tyvek bag of step (14) was put in the freezing dryer and frozen to −70° C. at the rate of −1° C. per minute, and then dried under the vacuum of 5 torr for 24 hours to obtain a freeze-dried acellular dermal matrix.
(17) After freeze-drying, the freeze-dried acellular dermal matrix was sterilized in an E.O. gas sterilizer (HS-4313EO, HanShin Medical Co., Ltd., Korea).
(18) The sterilized, freeze-dried acellular dermal matrix was sealed in an aluminum bag and stored at room temperature until analysis experiments.

Comparative Example 1

An acellular dermal matrix was prepared with pig skin by using HBSS containing 7.5% dextran (MWT 70,000), 6% sucrose, 7.5% polyvinylpyrrolidone (MWT 40,000), 1.25% raffinose and 1 mM disodium ethylenediamine tetraacetic acid according to the same method disclosed in Example 1 of U.S. Pat. No. 5,336,616.

Comparative Example 2

A freeze-dried skin was prepared with pig skin according to the following steps.
(1) Pig skin was washed with saline solution.
(2) The pig skin was cut at the size of 5×10 cm$^2$.
(3) The pig skin was immersed in 1M NaCl (Sigma, USA) solution.
(4) A 38° C. incubator (P-039, CoreTech, Korea) was prepared.
(5) The reaction of the pig skin immersed in 1M NaCl (Sigma, USA) solution was carried out in the 38° C. incubator with stirring for about 6 to 24 hours.
(6) Epidermis was removed by using forceps.
(7) The dermis from which the epidermis has been removed was washed with phosphate-buffered saline (pH 7.2, Gibco, USA).
(8) The washed dermis was immersed in 0.1% SDS and reacted with stirring at room temperature for 1 hour to remove cells from the dermis.
(9) The dermis from which cells have been removed was washed with phosphate-buffered saline.
(10) Glycerol (Sigma, USA) and phosphate-buffered saline were mixed in the weight ratio of 1:9 to obtain a cryoprotectant.
(11) A low-temperature bath (P-039, CoreTech, Korea) was set at 4° C.
(12) The pig skin of step (9) was put in the 4° C. low-temperature bath, and then the cryoprotectant was penetrated into the pig skin for 12 hours.
(13) The penetration-completed pig skin and 50 ml of the cryoprotectant were put in a Tyvek bag (Korea C&S Co., Ltd., Korea).
(14) A freezing dryer (Genesis 25XL, VirTis, USA) was prepared.
(15) The Tyvek bag of step (13) was put in the freezing dryer and frozen to −70° C. at the rate of −1° C. per minute, and then dried under the vacuum of 5 torr for 24 hours to obtain a freeze-dried acellular dermal matrix.
(16) After freeze-drying, the freeze-dried acellular dermal matrix was sterilized in an E.O. gas sterilizer (HS-4313EO, HanShin Medical Co., Ltd., Korea).
(17) The sterilized, freeze-dried acellular dermal matrix was sealed in an aluminum bag and stored at room temperature until analysis experiments.

Experimental Example 1

Histological Examination

H&E (hematoxylin & eosin) staining was carried out as follows:
(1) A paraffin block was cut with 4 μm thickness and dried to obtain a paraffin section.
(2) For deparaffinization, after conducting xylene treatment of 5 minutes three times, 100% ethanol treatment of 2 minutes three times, 90% ethanol treatment of 1 minute one time, 80% ethanol treatment of 1 minute one time and 70% ethanol treatment of 1 minute one time, the section was rinsed in running water for 10 minutes.
(3) After staining with hematoxylin for 10 minutes, the section was rinsed in running water for 3 minutes. Then, after staining with eosin for 10 minutes, the section was rinsed in running water until no eosin was detected in the rinse water. After conducting 70% ethanol treatment of 1 second ten times, 80% ethanol treatment of 1 second ten times, 90% ethanol treatment of 1 second ten times, 100% ethanol treatment of 1 minute two times and xylene treatment of 3 minutes three times, the section was mounted with a mounting solution.

The scanning electron microscopy observation was carried out as follows:

(1) A specimen was pre-fixed with 2.5% glutaraldehyde solution (fixative solution) for 2 hours, washed with 0.1M phosphate-buffered saline and post-fixed with 1% $OsO_4$ solution.

(2) The fixed specimen was hydrated and substituted through a series of increased ethanol concentration, and the specimen was then frozen and fractured in −190° C. liquid nitrogen to expose the cross section, and completely dried by using a critical point dryer (HCP-2).

(3) The specimen was fixed at an aluminum stub (specimen mount) with the fractured surface upward, and metal coated with Pt—Pd at about 10 mm thickness by using a metal ion coating system (E-1030 ion sputter).

(4) The specimen was observed and photographed with a scanning electron microscope (Hitachi S-4700, Japan).

The freeze-dried acellular dermal matrixes were prepared according to the method of Example by using a cryoprotectant comprising sucrose in the final concentration of 5%, 10%, 15%, 20%, 25% and 30% by weight. The prepared acellular dermal matrixes were rehydrated, and were then stained with H&E and photographed with an optical microscope (Olympus BX51). The results are represented in FIG. 1. When the concentration of sucrose is less than 20% by weight, the matrix of tissue is destroyed in proportion to the concentration after freeze-drying. However, in the case that sucrose concentration is 20%, 25% and 30% by weight, the matrix of tissue is not destroyed in proportion to the concentration of sucrose and maintains morphology close to the original structure.

Figure 2:
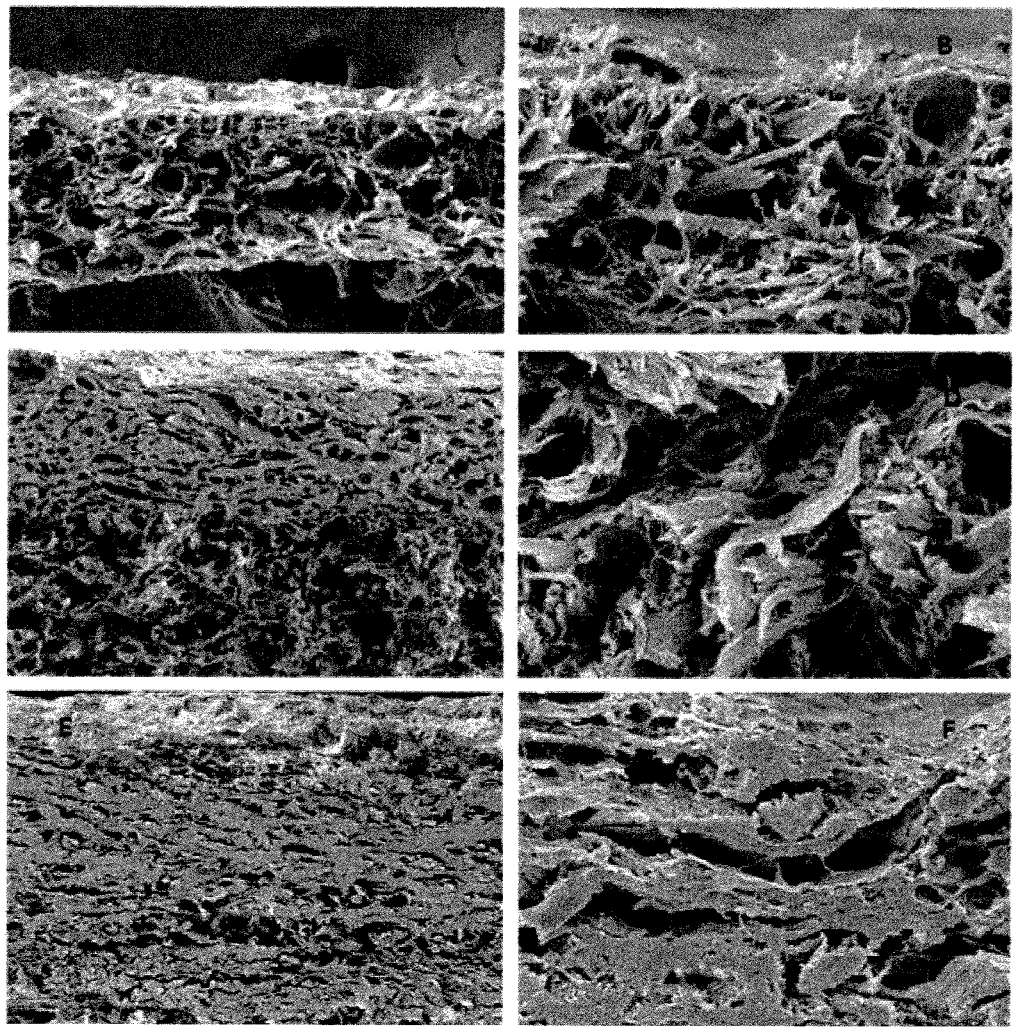
FIG. 2 is scanning electron microscope photographs of acellular dermal matrix freeze-dried with a cryoprotectant using each concentration of sucrose with 150× and 1,000× magnifications. (A: 0% sucrose, 150×; B: 0% sucrose, 1,000×; C: 10% sucrose, 150×; D: 10% sucrose, 1,000×; E: 30% sucrose, 150×; F: 30% sucrose, 1,000×)

In addition, the acellular dermal matrix prepared by using a cryoprotectant not containing sucrose and the acellular dermal matrixes prepared as above by treating with a cryoprotectant containing 10% and 30% by weight of sucrose were photographed with a scanning electron microscope according to the above method. The results are represented in FIG. 2. In the groups treated with a cryoprotectant not containing sucrose and containing 10% by weight of sucrose, the acellular dermal matrixes are destroyed after freeze-drying. Contrary to this, the acellular dermal matrix treated with a cryoprotectant containing 30% by weight of sucrose shows that its morphology is well maintained after freeze-drying without destroying matrix of tissue.

From the above results, it can be known that in the acellular dermal matrix treated with a cryoprotectant containing 20% by weight or more of sucrose the destruction of tissue that occurred in the course of freeze-drying is remarkably reduced.

Figure 3:
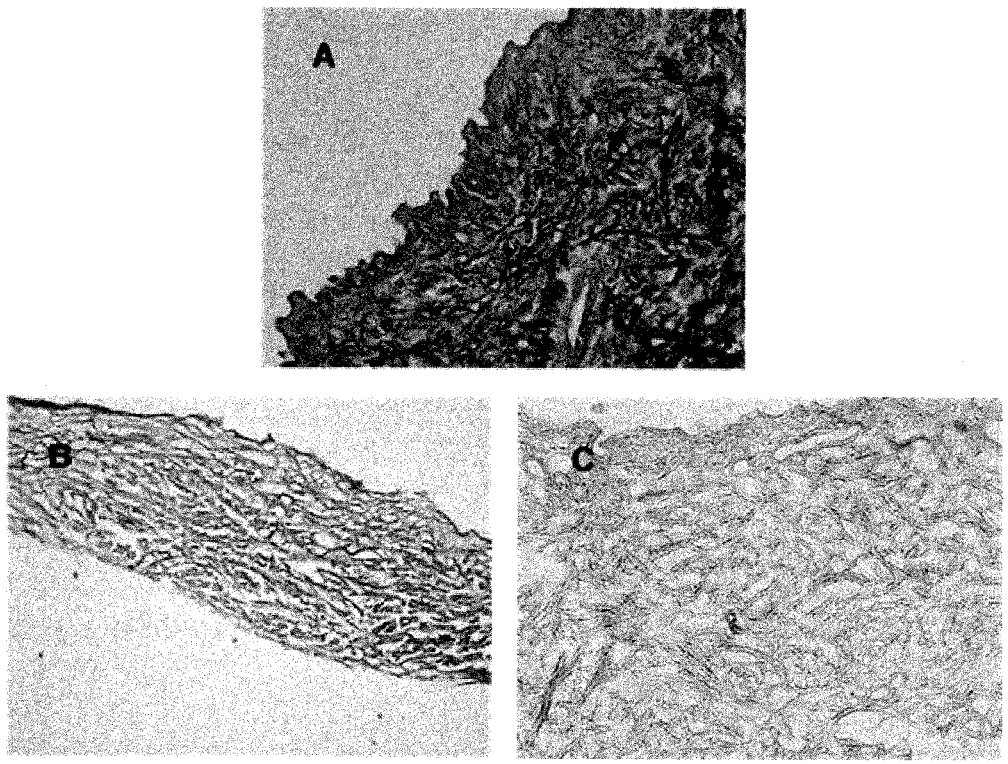
FIG. 3 is optical microscope photographs of acellular dermal matrixes of Example and Comparative Examples 1 and 2 with 100× magnification. (A: Example; B: Comparative Example 1; C: Comparative Example 2)

The acellular dermal matrixes of Example and Comparative Examples 1 and 2 were stained with H&E and then photographed with an optical microscope (Olympus BX51) according to the above method. The results are represented in FIG. 3.

By means of the excellence of the cryoprotectant, the acellular dermal matrix of Example shows much better stability of tissue by preventing tissue from destruction in the course of freeze-drying as compared with the acellular dermal matrixes of Comparative Examples 1 and 2.

Experimental Example 2

Measurement of Degradability by Collagenase

To evaluate the stability of acellular dermal matrixes of Example and Comparative Examples 1 and 2, the degradability by collagenase was measured as follows:

(1) 25 mg of sample was added to 5 mM TES buffer containing 0.36 mM calcium chloride and mixed well.

(2) 0.1 ml of collagenase (0.1 mg/ml) was added to the sample of step (1) and incubated at 37° C. for one day with stirring.

(3) 4.0 mM L-leucine standard solution was serially diluted and treated with ninhydrin color reagent. A standard curve was prepared by measuring absorbance at 570 nm (VERSA max, Molecular Device, USA).

(4) The sample of step (2) was treated with ninhydrin color reagent and absorbance at 570 nm was then measured.

(5) The amount of released L-leucine from each sample was calculated by using the L-leucine standard curve of step (3).

Figure 4:
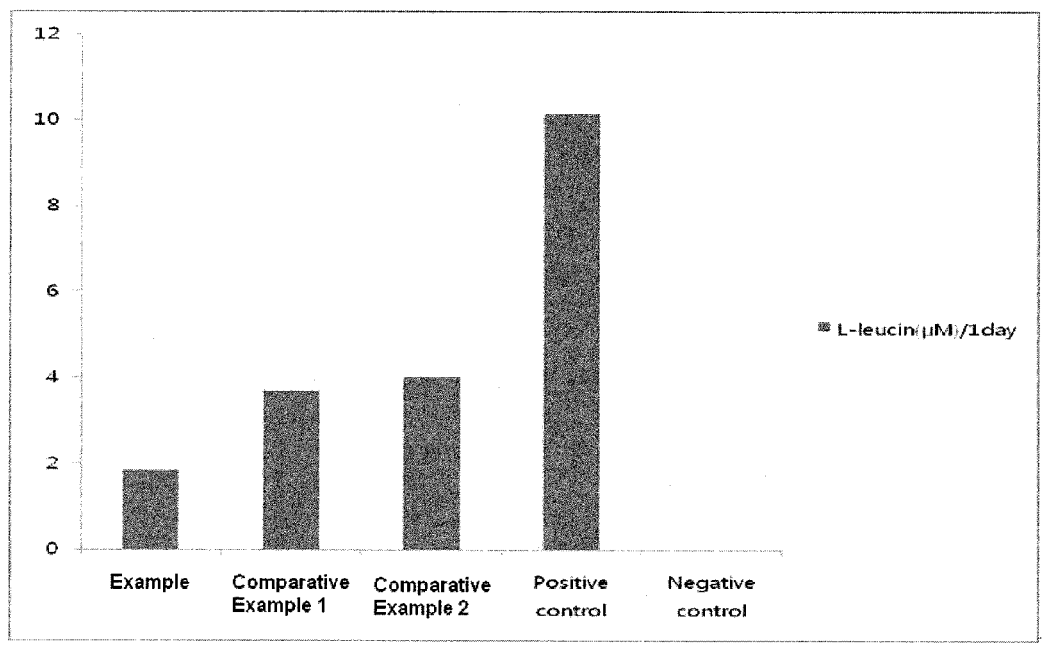
FIG. 4 is a graph representing results of degradability measured by the treatment of acellular dermal matrix which is processed with cryoprotectants comprising sucrose in the final concentration of 30% by weight, and acellular dermal matrixes of Comparative Examples 1 and 2 with collagenase. (Positive control: treatment of collagen powder with collagenase; Negative control: No treatment of collagenase)

The above calculated L-leucine release amount is represented in FIG. 4. As can be seen from FIG. 4, the acellular dermal matrix of Example shows higher stability of tissue as compared with the acellular dermal matrixes of Comparative Examples 1 and 2 so that degradation rate by collagenase is remarkably reduced.

From histological analysis via microscope photograph or measurement of degradability by collagenase, it can be known that the processing method according to the present invention provides high stability of tissue compared with conventional methods. As a result, an acellular dermal matrix according to the present method can increase the success rate of grafting and curtail the treatment duration since its extracellular matrix and basement membrane are well maintained without impairment, and the change of biological properties is minimized.

The invention claimed is:

1. A method for preparing an acellular dermal matrix comprising the steps of:
   i) removing epidermis of an isolated allogeneic skin;
   ii) removing cells in dermis of the epidermis-removed skin;
   iii) mixing a cryoprotectant to include glycerol, propylene glycol, sucrose and a basic solvent or solution, wherein the mixing ratio of glycerol, propylene glycol and the basic solvent or solution is 0.8-1.5:0.8-1.5:7-9 based on weight, and
   the cryoprotectant contains sucrose in an amount ranging from 25% to 40% by weight of the cryoprotectant;
   iv) penetrating the cryoprotectant into the skin from which epidermis and cells in dermis are removed; and
   v) freeze-drying the cryoprotectant-penetrated skin at a freezing rate of from −0.1 to −5° C. per minute to obtain an acellular dermal matrix.

2. The method for preparing an acellular dermal matrix according to claim 1, wherein the basic solvent or solution is one or more selected from the group consisting of distilled water, normal saline, PBS (phosphate-buffered saline), HBSS (Hank's balanced salt solution), TBS (Tris-buffered saline), TAPS (N-Tris(hydroxymethyl)methyl-3-aminopropanesulfonic acid) buffer, Bicine (N,N-Bis(2-hydroxyethyl) glycine) buffer, HEPES (4-(2-hydroxyethyl)-1-piperazineethanesulfonic acid) buffer, TES (N-Tris (hydroxymethyl)methyl-2-aminoethanesulfonic acid) buffer, PIPES (piperazine-N,N'-bis(2-ethanesulfonic acid) buffer, cacodylate buffer, MES (2-(N-morpholino)ethanesulfonic acid) buffer, MEM (Minimum Essential Media), DMEM (Dulbecco's Modified Eagle Media), RPMI 1640, IMDM (Iscove's Modified Dulbecco's Media), Defined Keratinocyte-SFM, Keratinocyte SFM, KnockOut D-MEM, AminoMAX-II Complete Medium and AminoMAX-C100 Complete Medium.

3. The method for preparing an acellular dermal matrix according to claim 1, wherein the final concentration of sucrose in the cryoprotectant is 30% by weight.

4. The method for preparing an acellular dermal matrix according to claim 1, wherein the cryoprotectant is penetrated into the separated skin in a 4° C. low temperature bath for 6 to 24 hours.

5. The method for preparing an acellular dermal matrix according to claim 1, wherein the cryoprotectant-penetrated skin is frozen at a freezing rate of −1° C. per minute.

* * * * *